(12) United States Patent
Walsworth et al.

(10) Patent No.: US 9,804,239 B2
(45) Date of Patent: Oct. 31, 2017

(54) NUCLEAR SINGLET STATES AS A CONTRAST MECHANISM FOR NMR SPECTROSCOPY

(71) Applicant: President and Fellows of Harvard College, Cambridge, MA (US)

(72) Inventors: Ronald L. Walsworth, Newton, MA (US); Stephen J. Devience, Cambridge, MA (US); Matthew S. Rosen, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 490 days.

(21) Appl. No.: 14/380,919

(22) PCT Filed: Feb. 28, 2013

(86) PCT No.: PCT/US2013/028246
§ 371 (c)(1),
(2) Date: Aug. 25, 2014

(87) PCT Pub. No.: WO2013/130756
PCT Pub. Date: Sep. 6, 2013

(65) Prior Publication Data
US 2015/0042331 A1    Feb. 12, 2015

Related U.S. Application Data

(60) Provisional application No. 61/604,658, filed on Feb. 29, 2012.

(51) Int. Cl.
*G01V 3/00*    (2006.01)
*G01R 33/465*  (2006.01)
(Continued)

(52) U.S. Cl.
CPC .......... *G01R 33/465* (2013.01); *G01N 24/08* (2013.01); *G01R 33/32* (2013.01); *G01R 33/4608* (2013.01); *G01R 33/4616* (2013.01)

(58) Field of Classification Search
USPC ........................................... 324/309
See application file for complete search history.

(56) References Cited

U.S. PATENT DOCUMENTS

| | | | |
|---|---|---|---|
| 2009/0039883 A1* | 2/2009 | Bodenhausen | G01R 33/46 324/307 |
| 2011/0001475 A1* | 1/2011 | Vasos | G01R 33/282 324/307 |

(Continued)

OTHER PUBLICATIONS

Birken, D. L. et al., "N-Acetyl-L-aspartic acid: a literature review of a compound prominent in 1H0NMR spectroscopic studies of brain," Neuroscience and Biobehavioral Reviews, vol. 13, pp. 23-31 (1989).

(Continued)

*Primary Examiner* — Rodney Fuller
(74) *Attorney, Agent, or Firm* — Wilmer Cutler Pickering Hale and Dorr LLP

(57) ABSTRACT

Methods and systems for Nuclear Magnetic Resonance (NMR) spectra of complex chemical mixtures are described. The methods and systems allow undesired NMR spectral background to be removed or suppressed and target spectral peaks to be uncovered, for example, when strong background signals overlap weaker peaks. In some embodiments, the methods and systems employ a quantum filter utilizing nuclear spin singlet states.

29 Claims, 8 Drawing Sheets

(51) Int. Cl.
G01N 24/08 (2006.01)
G01R 33/46 (2006.01)
G01R 33/32 (2006.01)

(56) References Cited

U.S. PATENT DOCUMENTS

| | | | | |
|---|---|---|---|---|
| 2011/0050228 A1* | 3/2011 | Levitt | ............... | G01R 33/282 |
| | | | | 324/310 |
| 2011/0274626 A1* | 11/2011 | Duckett | ............... | A61K 49/10 |
| | | | | 424/9.361 |
| 2012/0326717 A1* | 12/2012 | Weitekamp | ......... | G01R 33/4608 |
| | | | | 324/301 |
| 2014/0012129 A1* | 1/2014 | Lohman | ............. | G01R 33/5601 |
| | | | | 600/420 |
| 2014/0112870 A1* | 4/2014 | Waddell | ............... | A61K 49/06 |
| | | | | 424/9.3 |

OTHER PUBLICATIONS

Choi, C. et al., "Measurement of brain glutamate and glutamine by spectrally-selective refocusing at 3 Tesla," Magnetic Resonance in Medicine, vol. 55, No. 5, pp. 997-1005 (May 2006).

Choi, C. et al., "Proton spectral editing for discrimination of lactate and threonine 1.31 ppm resonances in human brain in vivo," Magnetic Resonance in Medicine, vol. 56, No. 3, pp. 660-665 (Sep. 2006).

Cudalbu, C. et al., "Metabolite Concentration Estimates in the Rat Brain by Magnetic Resonance Spectroscopy Using QUEST and Two Approaches to Invoke Prior Knowledge," IEEE Proc. ProRISC, Veldhoven, Netherlands, pp. 609-614 (2005).

DeVience, S. J. et al., "Nuclear spin singlet states as a contrast mechanism for NMR spectroscopy," NMR in BioMedicine, 9 pages (2013).

DeVience, S. J. et al., "SUCCESS: Suppression of Undesired Chemicals using Contrast-Enhancing Singlet States," Proceedings of the 53rd Experimental Nuclear Magnetic Resonance Conference, Miami, Florida, 1 page (Apr. 15, 2012).

Ghosh, R. K. et al., "Measurements of the Persistent Singlet State of $N_2O$ in Blood and Other Solvents—Potential as a Magnetic Tracer," Magnetic Resonance in Medicine, vol. 66, No. 4, pp. 1177-1180 (Oct. 16, 2011).

Hu, J. et al., "Simultaneous Detection of Resolved Glutamate, Glutamine, and γ-Aminobutyruc Acid at 4 Tesla," Journal of Magnetic Resonance, vol. 185, No. 2, pp. 204-213, 18 pages (Apr. 2007).

International Search Report and Written Opinion issued by the European Patent Office as International Searching Authority for International Application No. PCT/US2013/028246 dated May 17, 2013 (16 pages).

Lee, H. K. et al., "Homonuclear J-refocused spectral editing technique for quantification of glutamine and glutamate by $^1H$ NMR spectroscopy," Magnetic Resonance in Medicine, vol. 34, No. 2, pp. 253-259 (Aug. 1995).

Levitt, Malcolm H., "Singlet Nuclear Magnetic Resonance," Annual Review of Physical Chemistry, vol. 63, No. 1, pp. 89-105, 20 pages (May 5, 2012).

Mason, G. F. et al., "Detection of brain glutamate and glutamine in spectroscopic images at 4.1 T," Magnetic Resonance in Medicine, vol. 32, No. 1, pp. 142-145 (Jul. 1994).

Pileio, G. and Levitt, M. H., "Isotropic filtering using polyhedral phase cycles: Application to singlet state NMR," Journal of Magnetic Resonance, vol. 191, pp. 148-155 (2008).

Pileio, G. and Levitt, M. H., "Theory of long-lived nuclear spin states in solution nuclear magnetic resonance. II. Singlet spin locking," The Journal of Chemical Physics, vol. 130, XP009134470, pp. 214501-1-214501-14 (2009).

Ross, B. and Bluml, S., "Magnetic Resonance Spectroscopy of the Human Brain," The Anatomical Record (New Anat.), vol. 265, pp. 54-84 (2001).

Sarchielli, P. et al., "Absolute quantification of brain metabolites by proton magnetic resonance spectroscopy in normal-appearing white matter of multiple sclerosis patients," Brain, vol. 122, pp. 513-521 (1999).

Schubert, F. et al., "Glutamate concentrations in human brain using single voxel proton magnetic resonance spectroscopy at 3 Tesla," Neuroimage., vol. 21, No. 4, pp. 1762-1771 (Apr. 2004).

Snyder, S. R. et al., "Two-Dimensional Zero-Quantum Coherence H NMR Spectroscopy of Glutamate and Glutamine," Proceedings of the International Society for Magnetic Resonance in Medicine, vol. 16, p. 1564 (2008).

Thompson, R. B. and Allen, P. S., "A new multiple quantum filter design procedure for use on strongly coupled spin systems found in vivo: Its application to glutamate," Magnetic Resonance in Medicine, vol. 39, No. 5, pp. 762-771 (May 1998).

Thompson, R. B. and Allen, P. S., "Response of metabolites with coupled spins to the STEAM sequence," Magnetic Resonance in Medicine, vol. 45, No. 6, pp. 955-965 (Jun. 2001).

Vasos, P. R. et al., "Long-lived states to sustain hyperpolarized magnetization," Proc. Natl. Acad. Sci. USA, vol. 106, No. 44, pp. 18469-18473 (Nov. 3, 2009).

Wallwork, J. C. and Sandstead, H. H., "Effect of Zinc Deficiency on Appetite and Free Amino Acid Concentrations in Rat Brain," Journal of Nutrition, vol. 113, pp. 47-54 (1983).

Yang, S. et al., "Spectral simplification for resolved glutamate and glutamine measurement using a standard STEAM sequence with optimized timing parameters at 3, 4, 4.7, 7, and 9.4T," Magnetic Resonance in Medicine, vol. 59, No. 2, pp. 236-244 (Feb. 2008).

* cited by examiner

NUCLEAR SINGLET STATES AS A CONTRAST MECHANISM FOR NMR SPECTROSCOPY

CROSS-REFERENCE TO RELATED APPLICATIONS

This application is a national stage application of International Application No. PCT/US13/28246 entitled "Nuclear Singlet States as a Contrast Mechanism for NMR Spectroscopy," filed Feb. 28, 2013, which claims the benefit of the priority of U.S. Provisional Application No. 61/604,658 entitled "Nuclear Singlet States as a Contrast Mechanism for NMR (Nuclear Magnetic Resonance) Spectroscopy," filed Feb. 29, 2012, which is incorporated by reference in its entirety.

FIELD OF THE INVENTION

The invention relates generally to the field Nuclear Magnetic Resonance (NMR). In particular, the invention relates to techniques utilizing nuclear spin singlet states, e.g., for creating contrast enhancement in NMR spectroscopy.

BACKGROUND

Nuclear magnetic resonance (NMR) spectroscopy provides a quantitative, non-destructive measure of chemical concentrations in complex mixtures both in vitro and in vivo. In many samples, the spectral lines are narrow while the range of resonance frequencies is broad, and there is little overlap of spectral lines.

Nuclear magnetic resonance spectra of complex chemical mixtures often contain, however, unresolved and unseen spectral components, especially when a strong background spectrum overlaps weaker peaks. For example, mixtures of biomolecules, such as blood, urine, and brain tissue, often contain a large number of compounds with spectral lines mostly overlapped by a few dominant metabolites. Furthermore, some abundant metabolites, such as glutamine and glutamate, have such similar structures that their spectra are nearly identical and are difficult to resolve from one another. In all these cases, no amount of signal averaging can improve the resolution.

While improved resolution can be achieved using higher-field instruments, this is often a costly solution. An alternative is to use quantum filters to remove undesired spectral components and to select those of interest. These techniques work by creating a quantum coherence on a target molecule and then applying phase cycling or gradient filters to selectively suppress either the target or the background signals. Common applications include water and fat suppression as well as metabolite-specific enhancement in magnetic resonance amino-acid-specific enhancement in the spectroscopy of proteins, and metabolic analysis of blood and urine. However, quantum filters have had limited success in differentiating molecules with very similar structures, such as glutamine and glutamate.

SUMMARY OF THE INVENTION

This invention is based, in part, on the discovery that that nuclear spin singlet states are preserved by RF (radiofrequency) spin locking, while other spin states are driven to saturation.

It is understood that any of the embodiments described below can be combined in any desired way, and any embodiment or combination of embodiments can be applied to each of the aspects described below.

In one aspect, the invention provides a method comprising: (a) selectively creating a nuclear spin singlet state in a target molecule, so as to detect presence of the target molecule within a sample, wherein the sample contains a mixture of molecules and includes at least some background molecules that are different from the target molecule; and (b) preserving spin polarization of the singlet state while saturating the spin magnetizations of background molecules, so as to suppress spectroscopic signals from the background molecules and to enhance spectroscopic contrast between the target molecule and the background molecules.

In some embodiments, the act of selectively creating the nuclear spin singlet state comprises: applying to the target molecule a sequence of pulses having parameters that are optimized so as to achieve the desired nuclear spin singlet state in the target molecule while minimizing singlet nature of the nuclear spin states of the background molecules.

In some embodiments, the method further comprises converting the spin polarization of the singlet state back to transverse magnetization for signal readout, by controllably applying RF (radiofrequency) pulses.

In some embodiments, the act of preserving spin polarization of the singlet state while saturating spin magnetization of the background molecules comprises: applying a substantially continuous spin-locking RF field.

In some embodiments, the act of saturating spin magnetization of background molecules comprises: using a polyhedral, spherically symmetric phase cycle that substantially removes non-singlet signals.

In some embodiments, the NMR spectrum of the target molecule is similar to, and substantially overlaps with, the NMR spectrum of the background molecules.

In some embodiments, the target molecule is one of: aspartate, threonine, and glutamine. In one embodiment, the target molecule is aspartate. In another embodiment, the target molecule is threonine. In still another embodiment, the target molecule is glutamine.

In some embodiments, the background molecules comprise at least one of: N-acetylaspartate, myo-inositol, and glutamate.

In some embodiments, the sequence of pulses is a pulse sequence depicted in FIG. 1A, 1B, 5A or 5B.

In another aspect, the invention provides an NMR (nuclear magnetic resonance) system, comprising: (a) an NMR transceiver including an RF generator configured to generate a sequence of RF fields that have controllable parameters; and (b) a controller configured to generate and relay a set of instructions to the transceiver to controllably apply the RF field sequence to a sample, so as to selectively create a nuclear spin singlet state in a target molecule, then preserve spin polarization of the singlet state while saturating the spin magnetizations of background molecules within the sample, thereby suppressing spectroscopic signals from the background molecules and enhancing spectroscopic contrast between the target and background molecules.

In some embodiments, the controller is further configured to optimize the parameters of the RF field sequence so as to convert the spin polarization of the singlet state back to transverse magnetization, for signal readout from the target molecule.

In some embodiments, the RF field sequence includes a spin-locking RF field that is resonant with the spins and is substantially continuous, and wherein the spin-locking RF field is applied after the nuclear spin singlet state has been selectively created in the target molecule, thereby preserving spin polarization of the singlet state while saturating spin magnetizations of the background molecules.

In some embodiments, the NMR spectrum of the target molecule is similar to, and substantially overlaps with, the NMR spectrum of the background molecules.

In some embodiments, the target molecule is aspartic acid and the background molecules comprise N-acetylaspartic acid, and wherein the optimized parameters of the RF field sequence comprise: transmit frequency v=385 Hz; chemical shift $\delta_{av}$=2.71 ppm; and singlet creation delay times $\tau_1$, $\tau_2$ and $\tau_3$ and relaxation delay time $\tau_4$, where $\tau_1$=9 ms (milliseconds), $\tau_2$=10.3 ms, $\tau_3$=11.5 ms, and $\tau_4$=1 sec.

In some embodiments, the target molecule is glutamine and the background molecules comprise glutamate, and wherein the optimized parameters of the RF field sequence comprise: transmit frequency v=385 Hz; chemical shift $\delta_{av}$=2.23 ppm; and singlet creation delay times $\tau_1$, $\tau_2$ and $\tau_3$, and relaxation delay time $\tau_4$; where $\tau_1$=22 ms (milliseconds), $\tau_2$=15 ms, $\tau_3$=11.1 ms, and $\tau_4$=500 ms.

In some embodiments, the target molecule is threonine and the background molecules comprise myo-inositol, and wherein the optimized parameters of the RF field sequence comprise: transmit frequency v=790 Hz; chemical shift $\delta_{av}$=3.87 ppm; and singlet creation delay times $\tau_1$, $\tau_2$ and $\tau_3$, and relaxation delay time $\tau_4$; where $\tau_1$=40 ms (milliseconds), $\tau_2$=52 ms, $\tau_3$=1.85 ms, and $\tau_4$=200 ms.

In some embodiments, the RF sequence is a pulse sequence depicted in FIG. 1A, 1B, 5A or 5B.

In some embodiments, the method further comprises applying the spin-locking RF field at an average resonance frequency of coupled protons in the target molecule.

In some embodiments, the method further comprises applying the spin-locking RF field at a frequency other than an average resonant frequency of coupled protons in the target molecule, so as to further enhance spectroscopic signals from the target molecule.

In yet another aspect, the invention provides a method comprising: (a) selectively creating a nuclear spin singlet state in a target spin, so as to detect presence of the target spin within a sample containing a mixture of spins; wherein the sample includes at least some background spins that are different from the target spin; and (b) preserving spin polarization of the singlet state while saturating the spin magnetizations of background spins, so as to suppress spectroscopic signals from the background spins and to enhance spectroscopic contrast between the target spin and the background spins.

In some embodiments, the sample contains at least one of: a protein; and a polymer.

In still another aspect, the invention provides an NMR (nuclear magnetic resonance) system, comprising: (a) an NMR transceiver including an RF generator configured to generate a sequence of RF fields having controllable parameters, and to apply the RF field sequence to a sample; wherein the sample contains a mixture of molecules, and includes at least some background molecules that are different from a target molecule; and (b) a controller configured to generate and optionally relay a set of instructions to the transceiver to selectively create a nuclear spin singlet state in the target molecule, then preserve spin polarization of the singlet state while saturating the spin magnetizations of the background molecules, thereby suppressing spectroscopic signals from the background molecules and enhancing spectroscopic contrast between the target molecule and the background molecules.

In some embodiments, the RF field sequence is a pulse sequence depicted in FIG. 1A, 1B, 5A or 5B.

In yet another aspect, the invention provides a system comprising: a computer readable medium including instructions that when executed cause an NMR transceiver including an RF generator to generate a sequence of RF fields to selectively create a nuclear spin singlet state in the target molecule, then preserve spin polarization of the singlet state while saturating the spin magnetizations of the background molecules, thereby suppressing spectroscopic signals from the background molecules and enhancing spectroscopic contrast between the target molecule and the background molecules.

DETAILED DESCRIPTION OF THE INVENTION

Figures 1A, 1B:
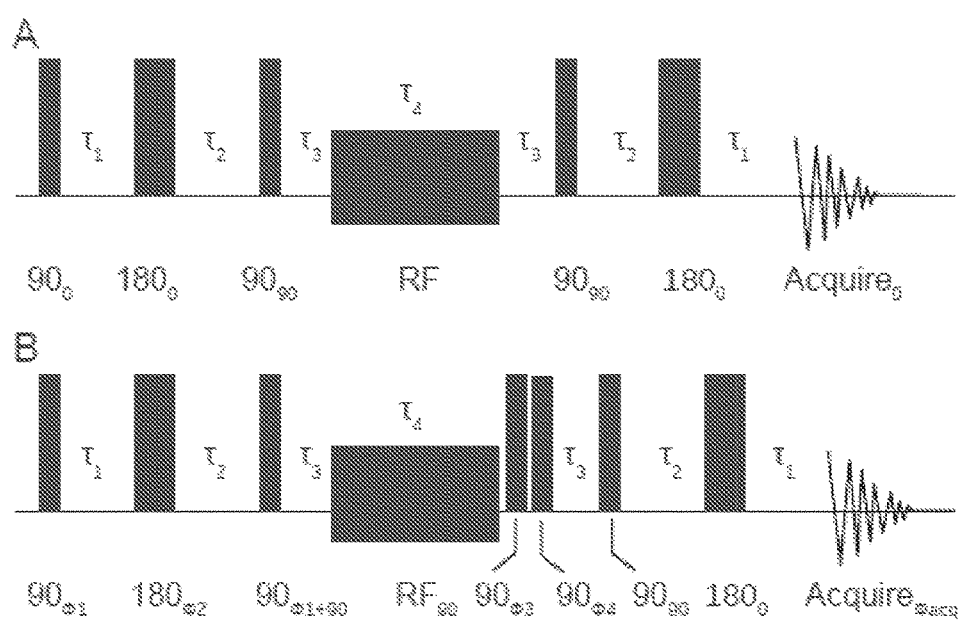
FIG. 1A illustrates a basic SUCCESS pulse sequence.
FIG. 1B illustrates an optimized SUCCESS pulse sequence.

The patent and scientific literature referred to herein establishes knowledge that is available to those of skill in the art. The issued U.S. patents, allowed applications, published foreign applications, and references that are cited herein are hereby incorporated by reference to the same extent as if each was specifically and individually indicated to be incorporated by reference.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values≥0 and ≤2 if the variable is inherently continuous.

In the present application, reference to an element in the singular is not intended to mean "one and only one" unless specifically so stated, but rather "one or more." All structural and functional equivalents to the elements of the various embodiments described throughout this disclosure, known or later come to be known to those of ordinary skill in the art, are expressly incorporated herein by reference.

As used herein, unless specifically indicated otherwise, the word "or" is used in the inclusive sense of "and/or" and not the exclusive sense of "either/or."

In the present application, methods and systems of quantum filtration have been developed utilizing the nuclear spin singlet state. In overview, a nuclear spin singlet state is created, with spin quantum numbers j=0, $m_s$=0, in a target molecule. A continuous RF field then applied to both preserve the singlet and saturate the magnetization from interfering molecules. The transfer of spin polarization to the singlet is highly controllable through pulse sequence parameters, so that spectral contrast can be achieved between molecules with very similar structures. In some embodiments, in vitro measurements have shown that the can improve detection of three molecules relevant to neuroscience: threonine, aspartate, and glutamate. Many other molecules may be detected using the methods and systems disclosed this application, as described further below. In some embodiments, this technique may be named SUCCESS, or "Suppression of Undesired Chemicals using Contrast-Enhancing Singlet States."

In some embodiments of the present application, nuclear singlet states have been selected and created on molecules containing pairs of coupled protons or pairs of coupled methylene groups. The multi-pulse sequence required to create and measure the singlet state produces strong contrast between molecules with similar structures, such as glutamine and glutamate, and aspartic acid and N-acetylaspartic acid. The technique also produces excellent suppression of molecules in which no singlet state can be created.

Current quantum filters utilize coherences comprised of angular momentum states projected along the z-axis, i.e., levels of $m_s$. For example, a double-quantum filter selects (or rejects) all double quantum coherences, which consist of two or more spins in an $m_s$=1 state. However, spins can also be combined to form new states with different values of total angular momentum, characterized by quantum number j. Such states are often encountered when the coupling between nuclei is much stronger than the difference between their resonance frequencies. For example, in the $H_2$ molecule, the nuclear spin states cannot be properly described by Zeeman eigenstates of the individual spins. Instead, the spins combine to form new states classified as singlet and triplet (not to be confused with singlet and triplet descriptions of peak structure): para-$H_2$ with j=0 and the singlet eigenstate $$|S_0\rangle=(|\uparrow\downarrow\rangle-|\downarrow\uparrow\rangle)/\sqrt{2},$$

and ortho-$H_2$, with j=1 and triplet eigenstates $$|T_-\rangle=|\uparrow\uparrow\rangle, |T_0\rangle=(|\uparrow\downarrow\rangle+|\downarrow\uparrow\rangle)/\sqrt{2}, \text{ and } |T_+\rangle=|\downarrow\downarrow\rangle$$

In the above notation ↑ represents a spin aligned with the applied magnetic field, $B_0$, while ↓ represents a spin that is anti-aligned.

Recent work has shown that even when spins are only weakly coupled naturally, singlet and triplet states can be created by applying a continuous RF field on-resonance with the spins, which produces a strong effective coupling. Measurements of singlets produced this way in a variety of molecules showed that the singlet component often possesses a lifetime many times longer than the spin-lattice relaxation time, $T_1$, due to its unique symmetry properties. On the other hand, both the triplet states and other uncoupled spins are driven to saturation more quickly than $T_1$ due to the RF irradiation. The long-lived singlets were subsequently used to measure exchange and dynamics on slow timescales that were previously inaccessible.

However, the disparate lifetime of the singlet states compared with others spins during RF irradiation suggests that strong contrast can be created between those molecules with singlets and those without singlets. In one embodiment of the present application, this can be achieved as shown in conjunction with FIG. 1.

Figures 1C, 1D:
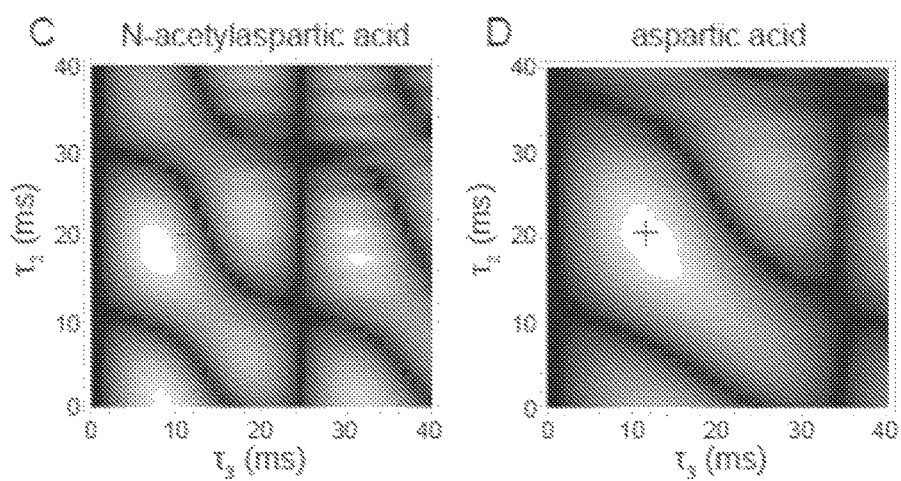
FIG. 1C illustrates a simulated NMR signal intensity map for N-acetylaspartic acid.
FIG. 1D illustrates a simulated NMR signal intensity map for aspartic acid.

FIG. 1 (including FIGS. 1A, 1B, 1C, and 1D) illustrates one example of a basic SUCCESS scheme, with the pulse sequence shown in FIG. 1A: (1) Prepare a target molecule in a singlet state, while minimizing singlet character in any other molecules; (2) Apply a resonant RF field to preserve the singlet state and drive all other spin states to saturation; (3) Convert the singlet polarization back into transverse magnetization for readout. The resulting spectrum should consist only of peaks from the spins that formed a singlet state.

FIG. 1A shows an embodiment of the SUCCESS pulse sequence: the NMR transmitter frequency $v_0$ (chemical shift $\delta_0$), is placed at the average resonance frequency of the two target nuclear spins, at a chemical shift $\delta_{av}$. Three pulses, with corresponding delays $\tau_1$, $\tau_2$, and $\tau_3$, create a population difference between singlet and triplet states on the target spins, described by the density matrix $\rho_{ST}=|S_0\rangle\langle S_0|-|T_0\rangle\langle T_0|$. Continuous RF spin-locking, also applied at the average resonance frequency of the target spins for time $\tau_4$, preserves the singlet state while driving other states toward saturation. Finally, two of the first three pulses are repeated in reverse order to return the remaining singlet population into transverse magnetization for readout.

FIG. 1B shows another embodiment of the SUCCESS pulse sequence, sometimes referred to as the "optimized" SUCCESS pulse sequence. To improve the suppression of non-singlet states, two filtering pulses are added as part of a spherically-symmetric phase cycle.

FIGS. 1C and 1D illustrate simulated NMR signal intensity maps for N-acetylaspartic acid and aspartic acid, which show that pulse sequence delays can be chosen to produce the singlet state selectively in one molecule and not in the other. The cross marks the parameters used in the demonstration in which aspartic acid was targeted. Parameters were chosen as a compromise between signal intensity and strong contrast. Higher contrast can be achieved with slightly longer values of $\tau_2$ and $\tau_3$, but with lower target signal intensity.

In real systems, the applied RF field contains a limited power across a limited bandwidth, so that saturation of the background spin systems is often incomplete. Background suppression can be improved using a polyhedral, spherically-symmetric phase cycle developed by Pileio et al., which removes all non-singlet signals (Pileio et al., (2008) *Journal of Magnetic Resonance* 191:148-155). The addition of phase cycling leads to the SUCCESS sequence shown in FIG. 1B.

Figures 5A, 5B:
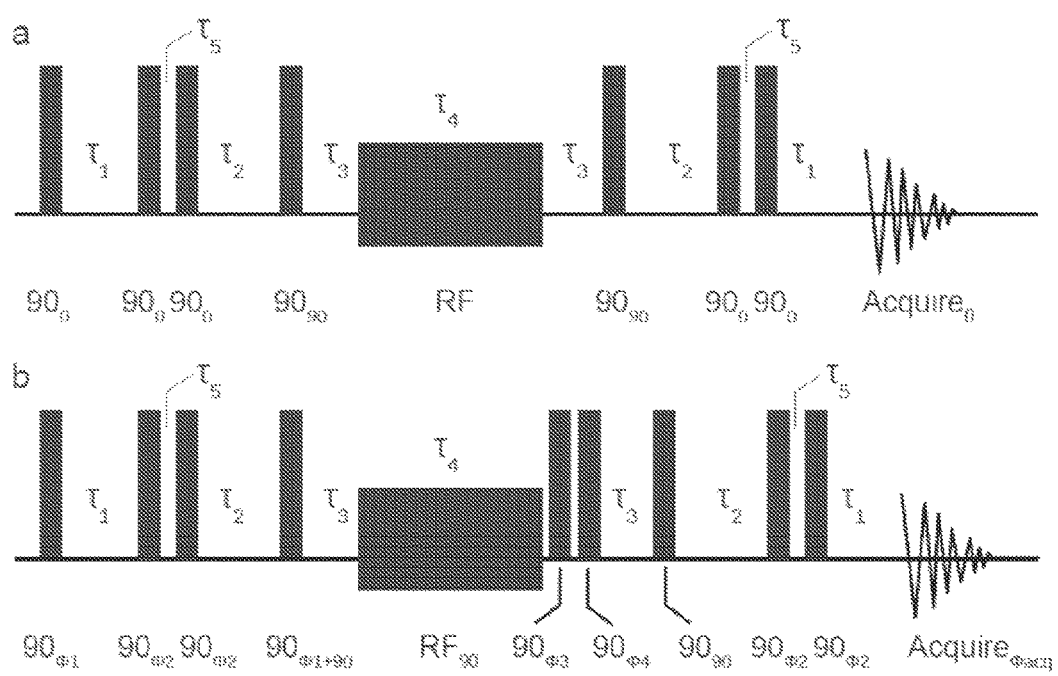
FIGS. 5A and 5B illustrate embodiments of a SUCCESS sequence with modified 180° pulses.

FIGS. 5A and 5B illustrate embodiments of the SUCCESS pulse sequence ("modified SUCCESS pulse sequence") having modified 180° pulses. Each 180° pulse has been split into two 90° pulses with a short delay between them. The purpose of this is to remove effects from another spin group coupled to our target spins. An example is the threonine molecule, where the $CH_3$ group couples to one of the two target spins. During the short delay between the 90° pulses, the $CH_3$ group precesses halfway through its cycle, which causes its effects on the target spins during delay $\tau_2$ to cancel the effects it had during $\tau_1$.

Figure 7:
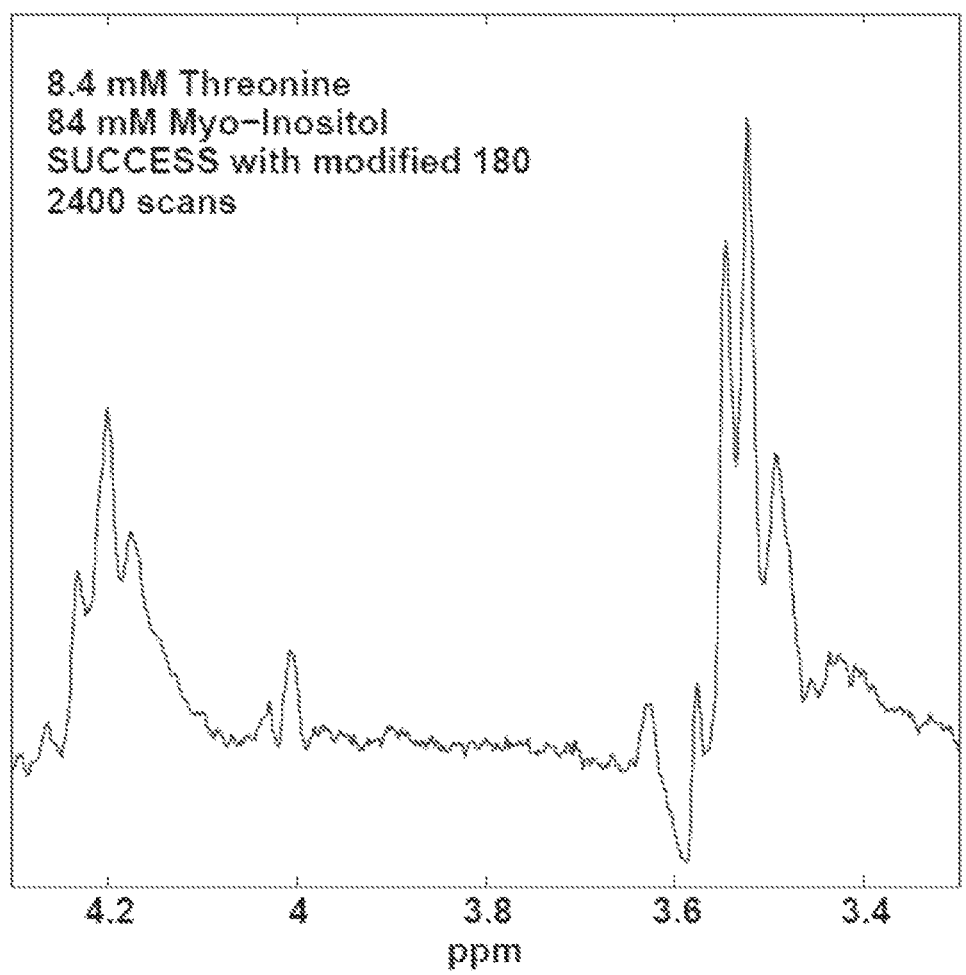
FIG. 7 illustrates a spectrum of threonine acquired with a SUCCESS sequence with a modified 180° pulse obtained with the pulse sequence of FIG. 5B.

Whereas with the normal SUCCESS sequence, about 12% of the threonine molecule's signal strength is generally recovered, with the modified SUCCESS sequence about 38% of the signal strength was recovered. This leads to a better signal-to-noise ratio and better suppression of background. For example, the spectrum shown in FIG. 7 was acquired with the modified sequence illustrated in FIG. 5B and shows improved signal-to-noise ratio relative to the spectrum shown in FIG. 3H.

One further complication is that background molecules may also contain singlet-producing groups with spectral components overlapping the target. Fortunately, the efficient preparation of a singlet state requires a pulse sequence with three properly-chosen delays that depend on the scalar-coupling and chemical shifts of each molecule. It was found that, through careful selection of these delays, a singlet can be created in the target molecule only. For example, the simulation results shown in FIGS. 1C and 1D show that by properly selecting $\tau_2$ and $\tau_3$, a large amount of singlet can be produced in aspartic acid while at the same time little singlet is produced in N-acetylaspartic acid.

In some embodiments of the present application, the SUCCESS technique was tested in vitro on three target molecules that are brain metabolites: aspartate, threonine, and glutamine. The spectra of these molecules are overlapped by peaks from N-acetylaspartate, myo-inositol, and glutamate, respectively. The test mixtures used in this embodiment are listed in Table 1. Each consists of a target molecule and an interfering background substance dissolved in a pH 7.0 phosphate buffer. The concentration ratios are based on typical values found in vivo, but the concentrations are higher. Control solutions were also created of each target and background molecule alone in pH 7.0 phosphate buffer. Reagents were purchased from Sigma Aldrich, St. Louis, Mo.

In one embodiment, NMR spectra are obtained using a Bruker 4.7 T vertical bore spectrometer with a 10 mm diameter BB probe. Data can be collected with XWINNMR software running on a Silicon Graphics $O_2$ computer. Other embodiments of the present application can use a wide variety of different spectrometers, probes, and computers or processors.

A transmitter power of 100 W can require a 90° pulse length of 26 μs and a 180° pulse length of 46 μs. Exponential apodization can be applied to all spectra with either 0.5 Hz or 1.0 Hz line-broadening constants. Spectra of the mixtures and controls can be first obtained by applying a 90° pulse and acquiring an FID. Spin-lattice relaxation times of the molecules can be measured in control solutions using an inversion recovery sequence. Measured J-couplings and peak positions of each molecule can be used to calculate optimal delays $\tau_1$, $\tau_2$, and $\tau_3$ for singlet creation on the target. Singlet lifetimes can be measured in the controls using the SUCCESS sequence in FIG. 1B by varying the relaxation delay $\tau_4$. A 24-phase cycle can be used with parameters provided in Table 2.

In one embodiment, a SUCCESS pulse sequence is then applied to each mixture, and the delays are experimentally optimized to produce the best contrast enhancement for the target molecule. Identical SUCCESS spectra can be acquired for control solutions.

The effectiveness of the quantum filter was quantified in terms of the contrast enhancement, or the ratio $$CE = \frac{C_S}{C_R} \qquad \text{Eq. (1)}$$

where $C_R$ is the contrast in a regular scan and $C_S$ is the contrast in a SUCCESS scan. The contrast is defined as the intensity of the target peak divided by the intensity of the interfering background peak.

In one embodiment, SUCCESS is tested on aspartic acid (ASP), which has a typical concentration of 3 mm in the brain. It contains a pair of protons, attached to a common carbon atom, whose long-lived singlet state has previously been investigated. Its acetylated form, N-acetylaspartic acid (NAA), also exists in the brain at a concentration 3-6 times higher. The geminal protons of interest in both molecules produce second-order spectral structure in the 2-3 ppm range, with further splitting caused by a third nearby proton, whose peak appears near 4 ppm. The spectrum of the mixture is dominated by NAA, and only the ASP peaks near 2.8 ppm are visible. After optimizing the SUCCESS delays to maximize the contrast, tests on the controls produce a SUCCESS spectrum with residual NAA magnetization of only 4% its original intensity. With the same delays, the SUCCESS spectrum of ASP appears similar to its conventional spectrum with a signal strength 25% its original intensity. The result is contrast enhancement of 6 or greater for all ASP peaks compared with NAA. The SUCCESS spectrum of the mixture appears nearly identical to that of ASP, except for the weak residual NAA magnetization near 2.5 ppm. Moreover, the water signal can be suppressed, e.g., by a factor of 6.5.

In another embodiment of the present application, the amino acid threonine (THR) is targeted. THR occurs at concentrations of around 500 μM in the brain. Threonine does not possess a pair of geminal protons, so the singlet must instead be created on the vicinal protons attached to carbons two and three. The target proton peaks lie near 3.6 and 4.2 ppm, and the downfield proton is strongly coupled to a methyl group ($\delta$=1.25 ppm), which gives it a multiplet splitting pattern.

The upfield target proton is overlapped by peaks from the common metabolite myo-inositol, which occurs in the brain at concentrations of 4-12 mM. At a 10:1 concentration ratio, the myo-inositol peaks completely cover the upfield threonine peak and makes it unresolvable in the spectrometer that was used. Even at a 1:1 concentration ratio the threonine peak is difficult to resolve. The optimized SUCCESS sequence can suppress the myo-inositol peaks to less than 0.7% of their original intensity, while preserving 12% of the threonine signal. The result is an average contrast enhancement of about 17 times. When applied to a sample with equal concentrations of threonine and myo-inositol (50 mM), the SUCCESS sequence can reduce the intensity of myo-inositol so greatly that only the threonine peak is evident. When performed on a sample containing 5 mM threonine and 50 mM myo-inositol, the resulting spectrum exhibits a threonine peak slightly more intense than myo-inositol, which allows the previously hidden peaks to be identified. The water peak can be suppressed by a factor of 32.

In yet another embodiment of the present application, SUCCESS is applied to a mixture of glutamine (GLN) and glutamate (GLU). The typical glutamate concentration is twice that of glutamine in the brain (8 mM and 4 mM respectively). These molecules have largely overlapping spectra that make individual measurements difficult, as well as similar chemical shifts and J-coupling strengths that make the application of quantum filters challenging. Accurate measurements of glutamine concentrations are difficult to obtain.

Each molecule contains two methylene groups that can be viewed as pairs of strongly-coupled, unresolvable protons. A third lone proton couples to one of the methylene groups. The spectra therefore exhibit a complex splitting pattern, with methylene group peaks between 1.8 and 2.6 ppm, and the lone proton peak at 3.7 ppm. A mixture of the two metabolites produces a spectrum with many poorly-resolved peaks, and the upfield methylene groups cannot be resolved at all.

Each methylene group is already strongly mixed into singlet and triplet states, but the resulting singlets cannot be easily manipulated for utilization in the quantum filter. Instead, a four-spin singlet state can be created by mixing the triplet states of the two methylene groups. This singlet is preserved by RF power just as in the case of a two-spin singlet, and it can be selectively created depending on the pulse-sequence parameters, but it does not possess an extended lifetime. Nevertheless, its symmetry allows it to pass through the polyhedral singlet filter. Lifetimes of 0.70±0.09 s and 0.80±0.1 s can be measured for this singlet in glutamate and glutamine, respectively. The singlet state lifetimes are shorter than the spin-lattice lifetimes of their constituent methylene groups. The measured $T_1$ times are 1.11±0.02 and 0.92±0.02 s for glutamate, and 1.24±0.05 and 1.01±0.04 s for glutamine.

In this embodiment, SUCCESS parameters are experimentally optimized to obtain high contrast for glutamine. The glutamate signal is suppressed so that only 0.86% of its original intensity remains. In contrast, 5.7% glutamine signal can be recovered, resulting in a contrast enhancement between 3 and 7 times. The SUCCESS spectrum of glutamine appears similar to the conventional spectrum, whereas that of glutamate mainly consists of a singlet peak that is poorly suppressed. The SUCCESS spectrum of the mixture appears very similar to that of glutamine, except for the residual glutamate peak at 2.3 ppm. This residual peak does not interfere with any glutamine peaks, and so the positions of the upfield methylene peaks of glutamine are now measureable. The water signal can be suppressed, e.g., by a factor of 13.

It was found that higher signal from glutamine could be obtained by moving the transmitter frequency approximately 40 Hz upfield from the average value, to $\delta_{av}=2.05$ ppm, and by applying a different set of delays. This created the same level of contrast while preserving 15% of the glutamine signal. Water suppression can also be higher, e.g., with a peak 38 times weaker than in a normal scan.

The nuclear spin singlet state has been considered as a state with a long lifetime and molecules containing singlets have been used to study slow dynamical processes and to store polarization for significant periods of time. Most singlet state experiments have used specially designed or selected molecules to produce singlet state lifetimes as long as possible. However, a singlet state can be prepared in nearly any coupled pair of protons. In many cases, surrounding spins will perturb the singlet and cause it to relax on the timescale $1/T_1$, but within this time the singlet exists as a unique quantum state that can be preserved and filtered.

In many ways this makes the singlet similar to other quantum coherences. Proton pairs can form double and zero-quantum coherences, which have both been used for a large number of quantum filters and applications. However, the singlet has the advantage of additional requirements for its creation and preservation. For example, three delays must be properly chosen rather than two for a typical zero-quantum coherence. Moreover, the preservation of the singlet requires RF power to be applied both at a proper resonance frequency and at sufficient intensity, which allows further control for targeting. For example, the RF spin-locking rate should be at least 5 times higher than the resonance frequency difference between target protons. Although there are concerns about the levels of RF power required for singlet preservation in vivo, it is believed that the technique can be adapted to magnetic resonance spectroscopy (MRS). By using lower magnetic fields, it should be possible to reduce the power to manageable levels.

The requirements for good singlet creation can also be a limitation. As the target proton pair is coupled to more surrounding protons in a molecule, the efficiency of singlet creation as well as the singlet purity decrease. In an ideal proton pair, 50% of the magnetization can be transferred into the singlet state, while the other half is transferred to $|T_0\rangle$. In aspartate, coupling to a third spin is around half the coupling strength between the singlet spins, and yet nearly 50% transfer can be achieved. However, in threonine, coupling with the neighboring methyl group is nearly the same strength as the coupling between the target protons. Simulations show that this reduces the amount of polarization transferred to the singlet to 25%.

It should also be considered that the highest contrast is not always achieved with the parameters that produce maximal target intensity. For example, myo-inositol contains inequivalent protons that can also pair up to form states with singlet character, and the best contrast for threonine is achieved when the delays minimize the amount of myo-inositol singlet created. With these parameters, only 20% of threonine polarization is transferred into singlet. Moreover, RF power must remain on for a sufficiently long time to let the system evolve and to saturate triplet states. During this time, there is some singlet relaxation. These various polarization losses mean that the contrast improvements afforded by SUCCESS come with a tradeoff in experiment time or imaging resolution. At best, compared with a regular scan, the SUCCESS sequence requires either at least four times more scans or voxels of twice the volume, to achieve the same signal to noise (S/N) ratio.

The SUCCESS quantum filtration technique utilizing singlet states can create strong and specific contrast enhancement in NMR spectroscopy, and it can improve the measurement of a number of brain metabolites, especially glutamine. Moreover, SUCCESS highlights the ubiquity of singlet states and demonstrates one of their applications other than extended-lifetime studies. The SUCCESS technique can be used to improve magnetic-resonance-based metabolic surveys and the diagnosis of disease without resorting to increasingly high-field spectrometers.

In the present disclosure, methods have been described that may include selectively creating a nuclear spin singlet state in a target molecule, so as to detect the presence of the target molecule within a sample that is being probed by NMR spectroscopy. The sample contains a mixture of molecules and includes at least some background molecules, which are different from the target molecule. In the present disclosure, the term "background molecule" means any molecule within a sample being probed that is different from the target molecule.

The methods may further include preserving spin polarization of the singlet state while saturating the spin magnetizations of the background molecules, so as to suppress spectroscopic signals from the background molecules and to enhance spectroscopic contrast between the target molecule and the background molecules.

As described above, a substantially continuous CW (continuous-wave) spin-locking RF field may be applied, in order to preserve spin polarization of the singlet state while saturating spin magnetization of the background molecules. In some embodiments, the CW RF field may be applied at the average resonance frequency of the spins of coupled protons in the target molecule. In other embodiments, the CW RF field may be applied at a frequency other than the average resonance frequency of the spins of coupled protons, so as to further enhance the spectroscopic signals (if any) from the target molecule.

In some embodiments, the sample may contain one or more proteins, one or more polymers, or some combination thereof.

In some embodiments, the sample contains a mixture of spins, and includes at least some background spins that are different from the target spin. In the present disclosure, the term "background spin" means any spin within a sample being probed that is different from the target spin.

In some embodiments, methods may be used that comprise selectively creating a nuclear spin singlet state in a target spin, so as to detect the presence of the target spin within a sample that contains a mixture of spins, and includes at least some background spins that are different from the target spin. The methods may further include preserving spin polarization of the singlet state while saturating the spin magnetizations of background spins, so as to suppress spectroscopic signals from the background spins and to enhance spectroscopic contrast between the target spin and the background spins.

In the embodiments described above, a NMR spectroscopic systems is used. As is well known, NMR systems typically include an NMR transceiver including an RF generator configured to generate a sequence of RF fields that have controllable parameters, and an NMR coil or other static B-field generator coupled to the NMR transceiver and configured to enclose a sample containing the molecules of interest.

In the embodiments described above, a NMR system may be used that includes a controller configured to optimize the parameters and to controllably apply the RF field sequence to a sample, thereby selectively creating a nuclear spin singlet state in a target molecule, then preserve spin polarization of the singlet state while saturating the spin magnetizations of background molecules within the sample. In this way, spectroscopic signals from the background molecules are suppressed, and spectroscopic contrast between the target and background molecules is enhanced.

The controller may be configured to generate and optionally relay a set of instructions to the transceiver to controllably apply the RF field sequence to a sample.

The controller may be further configured to optimize the parameters of the RF field sequence so as to convert the spin polarization of the singlet state back to transverse magnetization, for signal readout from the target molecule.

The controller may be any type of computer or processing system that is used to implement the methods, systems, and algorithms described in the present application, including but not limited to general purpose processors, PCs, and workstations. The methods and systems in the present application have not been described with reference to any particular programming language. It will be appreciated that a variety of platforms and programming languages may be used to implement the teachings of the present application. The processing system (or controller) may be selectively configured and/or activated by a computer program stored therein. Such a computer program may be stored in any computer readable storage medium.

The methods, systems and techniques presented in this disclosure can be applied to many other systems, including without limitation biofluids, chemical mixtures, and pharmaceutical drugs.

In some embodiments, the techniques and systems described herein are useful for spectroscopic analyses of samples that contain mixtures of compounds. In some embodiments, the compounds in the mixture have overlapping peaks in an NMR spectrum. In such instances, the techniques described herein can be applied to suppress or eliminate a spectral peak produced by one or more of the compounds in the mixture.

In some embodiments, the classes of applications that may be considered for SUCCESS include, without limitation, the following (classes I through VI):

I. Spectroscopy where SUCCESS may be used to distinguish overlapping spectral lines. This class may include, without limitation:
  a. Brain spectroscopy of metabolites and small molecules, including amino acids. Specific examples include, but are not limited to: (1) Glutamate, (2) Glutamine, (3) Threonine, (4) Aspartic Acid, (5) N-acetylaspartic Acid, (6) Serine, (7) Tyrosine and (8) Cysteine.
  b. Spectroscopy of other organs including heart, kidney, liver, lung, muscles, bone, etc.
  c. Spectroscopy of bodily fluids (in-vivo or in-vitro) such as whole blood, plasma, urine, cerebrospinal fluid, and others.
  d. Spectroscopy of food and beverages.
  e. Spectroscopy of hydrocarbons, such as crude oil and petrochemicals (e.g., hydrocarbon reservoir rock cores).
  f. Spectroscopy of pharmaceuticals, in-vivo and in-vitro.
  g. Spectroscopy of proteins.

II. Spectroscopy of rare or weak chemical compounds, where SUCCESS suppresses or enhances target signals or background signals.
  Example systems are the same as above for I.

III. Probe of molecular dynamics
  a. Measurement of spatial separation of singlet spins, measured through a decrease or increase in the SUCCESS signal.
    1. Diffusion of two spins in their environment.
    2. Changes in protein or nucleic acid conformation.

IV. Probe of molecular magnetic and electrical environment via singlet lifetimes and singlet state purity
  a. Molecular binding detected by decrease or increase of singlet signal due to:
    1. Ligand binding to proteins.
    2. Ligand binding to catalyst.
    3. Stacking of aromatic rings.
  b. Measurement of conformation changes in molecules, including protein or nucleic acid.

V. Nuclei: including, but not limited to, 1H, 31P, 19F, 13C, 15N, where the singlet is created on pairs of identical nuclei (i.e., 1H-1H) or different nuclei (i.e. 1H-19F).
  a. 31P compounds such as ATP, ADP, NAD, and NADP.
  b. 19F, 13C, and 15N in tracer compounds and drugs.
  c. 15N in DNA, nucleotides, purines, pyrimidines, histidine, arginine, and others.

VI. Imaging: where SUCCESS sequence is followed by or contained in a magnetic resonance imaging sequence.

a. Screening for brain small molecule deficiency or excess.

b. Time- and spatial-dependent monitoring of small molecule concentrations in the body following drug delivery or therapeutics.

In some embodiments, the techniques described herein are applied to low-field NMR spectrometers. Such low-field NMR spectrometers generally include instruments with magnetic field of 2 T or lower, e.g., 1.5 T, 1 T and 0.5 T. In general, techniques described can be used in NMR spectrometers operating at $^1$H Larmor frequencies between 400 MHz and 1 MHz, for example, at about 400 MHz, 350 MHz, 300 MHz, 250 MHz, 200 MHz, 150 MHz, 100 MHz, 50 MHz, 45 MHz, 42.5 MHz, 40 MHz, 35 MHz, 30 MHz, 25 Ml z, 20 MHz, 15 MHz, 10 MHz, 5 MHz, 4 MHz, 3 MHz, 2 MHz or 1 Mhz. Of course, these techniques can also be used in NMR spectrometers operating at 1H Larmor frequencies higher than 400 MHz. These techniques may be of particular interest for NMR spectrometers that do not require a cryo-cooled magnet for operation, e.g., bench-top or clinical NMR spectrometers.

In some embodiments, the techniques described herein can be used to generate a spectral library of compounds of interest that are present in a mixture.

In some embodiments, the techniques described herein can be used for process control. Process control includes monitoring reaction progress, sampling of batches for purity, presence of reactants or products, or quantitation of reactants, products, or intermediates. Such processes can be used in industrial processes, for example, in syntheses of petroleum products, biodiesel, and biopharmaceuticals. Techniques described herein can also be used by scientists for bench-top analysis of molecular structures, product purity, or reaction kinetics.

The techniques and systems disclosed herein may be implemented as a system or as a computer program product for use with a computer system or computerized electronic device. Such implementations may include a series of computer instructions, or logic, fixed either on a tangible medium, such as a computer readable medium (e.g., a diskette, CD-ROM, ROM, flash memory or other memory or fixed disk) or transmittable to a computer system or a device, via a modem or other interface device, such as a communications adapter connected to a network over a medium.

The medium may be either a tangible medium (e.g., optical or analog communications lines) or a medium implemented with wireless techniques (e.g., Wi-Fi, cellular, microwave, infrared or other transmission techniques). The series of computer instructions embodies at least part of the functionality described herein with respect to the system. Those skilled in the art should appreciate that such computer instructions can be written in a number of programming languages for use with many computer architectures or operating systems.

Furthermore, such instructions may be stored in any tangible memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The components, steps, features, objects, benefits and advantages that have been disclosed above are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages.

Nothing that has been stated or illustrated is intended to cause a dedication of any component, step, feature, object, benefit, advantage, or equivalent to the public. While the specification describes particular embodiments of the present application, those of ordinary skill can devise variations of the present application without departing from the inventive concepts disclosed in the disclosure.

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

EXAMPLES

SUCCESS Applied to Brain Metabolites

SUCCESS technique was applied in vitro on three target molecules that are important brain metabolites: aspartate, threonine, and glutamine. The spectral lines of these molecules are overlapped by peaks from N-acetylaspartate, myo-inositol, and glutamate, respectively. The test mixtures employed are listed in Table 1.

TABLE 1

| | Samples | | |
|---|---|---|---|
| Target Molecule | Target Concentration (mM) | Background Molecule | Background Concentration (mM) |
| aspartic acid | 3.0 | N-acetylaspartic acid | 11.4 |
| threonine | 50.0 | myo-inositol | 50.0 |
| threonine | 5.0 | myo-inositol | 50.0 |
| glutamine | 40.0 | Monosodium glutamate | 80.0 |

Each consisted of a target molecule and the interfering background substance dissolved in a pH 7.0 phosphate buffer with 69 mM total phosphate concentration. Metabolite concentrations were chosen to reflect typical ratios found in vivo but at higher absolute concentration. A control solution was created for each target and background molecule alone in the pH 7.0 phosphate buffer. Reagents were purchased from Sigma Aldrich, St. Louis, Mo.

$^1$H NMR spectra were obtained using a Bruker 4.7 T vertical bore spectrometer with a 10 mm diameter probe. Data were collected with XWINNMR software running on a Silicon Graphics $O_2$ computer. A transmitter power of 100 W required a 90° pulse length of 26 μs and a 180° pulse length of 46 μs. Exponential apodization was applied to all spectra with either 0.5 Hz or 1.0 Hz line-broadening constants. Spectra of the mixtures and controls were first obtained with a "one-pulse" sequence by applying a 90° pulse and acquiring an FID. Spin-lattice relaxation times of the molecules were measured in control solutions using an inversion recovery sequence. Measured J-couplings and peak positions of each molecule were used to calculate optimal delays $\tau_1$, $\tau_2$, and $\tau_3$ for the target spins by simulating the spin system with the Mathematica package *Spin-Dynamica* (Levitt (2011)—www.SpinDynamica.soton.ac.uk), and adjusting delays to maximize singlet state creation in the target and minimize singlet state creation in the background. For example, the simulation results shown in FIGS. 1C and 1D demonstrate that by properly selecting $\tau_2$ and $\tau_3$, large singlet state magnetization can be produced in aspartate while little singlet state is produced in N-acetylaspartate. Singlet lifetimes were measured in the controls using the SUCCESS sequence in FIG. 1B by varying the relaxation delay $\tau_4$. During $\tau_4$, spin locking was performed with a spin lock nutation rate $v_n$ such that $\tau_n > 5\Delta v$, where $\Delta v$ is the chemical shift splitting between the two target peaks. The 24-step phase cycle was used with parameters is provided in Table 2.

TABLE 2

24-step phase cycle used for SUCCESS

| Step | φ1 | φ3 | φ4 | φacq |
|---|---|---|---|---|
| 1 | 0 | 0 | 180 | 0 |
| 2 | 90 | 0 | 180 | 180 |
| 3 | 180 | 0 | 180 | 0 |
| 4 | 270 | 0 | 180 | 180 |
| 5 | 90 | 90 | 180 | 180 |
| 6 | 180 | 90 | 180 | 0 |
| 7 | 270 | 90 | 180 | 180 |
| 8 | 0 | 90 | 180 | 0 |
| 9 | 180 | 180 | 270 | 0 |
| 10 | 270 | 180 | 270 | 180 |
| 11 | 0 | 180 | 270 | 0 |
| 12 | 90 | 180 | 270 | 180 |
| 13 | 270 | 270 | 0 | 180 |
| 14 | 0 | 270 | 0 | 0 |
| 15 | 90 | 270 | 0 | 180 |
| 16 | 180 | 270 | 0 | 0 |
| 17 | 0 | 0 | 90 | 0 |
| 18 | 90 | 0 | 90 | 180 |
| 19 | 180 | 0 | 90 | 0 |
| 20 | 270 | 0 | 90 | 180 |
| 21 | 180 | 180 | 180 | 0 |
| 22 | 270 | 180 | 180 | 180 |
| 23 | 0 | 180 | 180 | 0 |
| 24 | 90 | 180 | 180 | 180 |

For both one-pulse and SUCCESS experiments, a delay of $5T_1$ was used between each scan to allow maximal recovery of magnetization. SUCCESS spectra were acquired of each mixture, and the delays were experimentally optimized to produce the best contrast enhancement for the target molecule. Identical SUCCESS spectra were acquired for control solutions. Each spectrum was normalized by dividing by the number of scans, N, so that the signal intensity per scan could be compared. More scans were used for SUCCESS experiments so that a sufficient signal-to-noise ratio (SNR) could be achieved for proper comparison with the one-pulse experiments. A large number of scans (on the order of thousands) were needed to achieve high SNR of the low-concentration solutions because of the low sensitivity of the 200 MHz spectrometer.

The effectiveness of the SUCCESS quantum filter was quantified in terms of the contrast enhancement of the target molecule's spectral peaks: i.e., the ratio $CE = C_S/C_R$, where $C_R$ is the contrast from a one-pulse experiment and $C_S$ is the contrast from a SUCCESS experiment. The contrast can be defined in two ways, using either (i) the peak intensities per scan of individual target spectral lines relative to the interfering background (undesired molecule) peak intensity per scan (also referred to as the peak contrast) or (ii) the integrated intensity per scan of all target lines relative to the integrated intensity per scan of the background (also referred to as the integrated contrast). For molecules with multiple peaks, the contrast was calculated (both peak and integrated) for each set of target and background peaks that overlap.

Figures 2A, 2B, 2C, 2D, 2E, 2F:
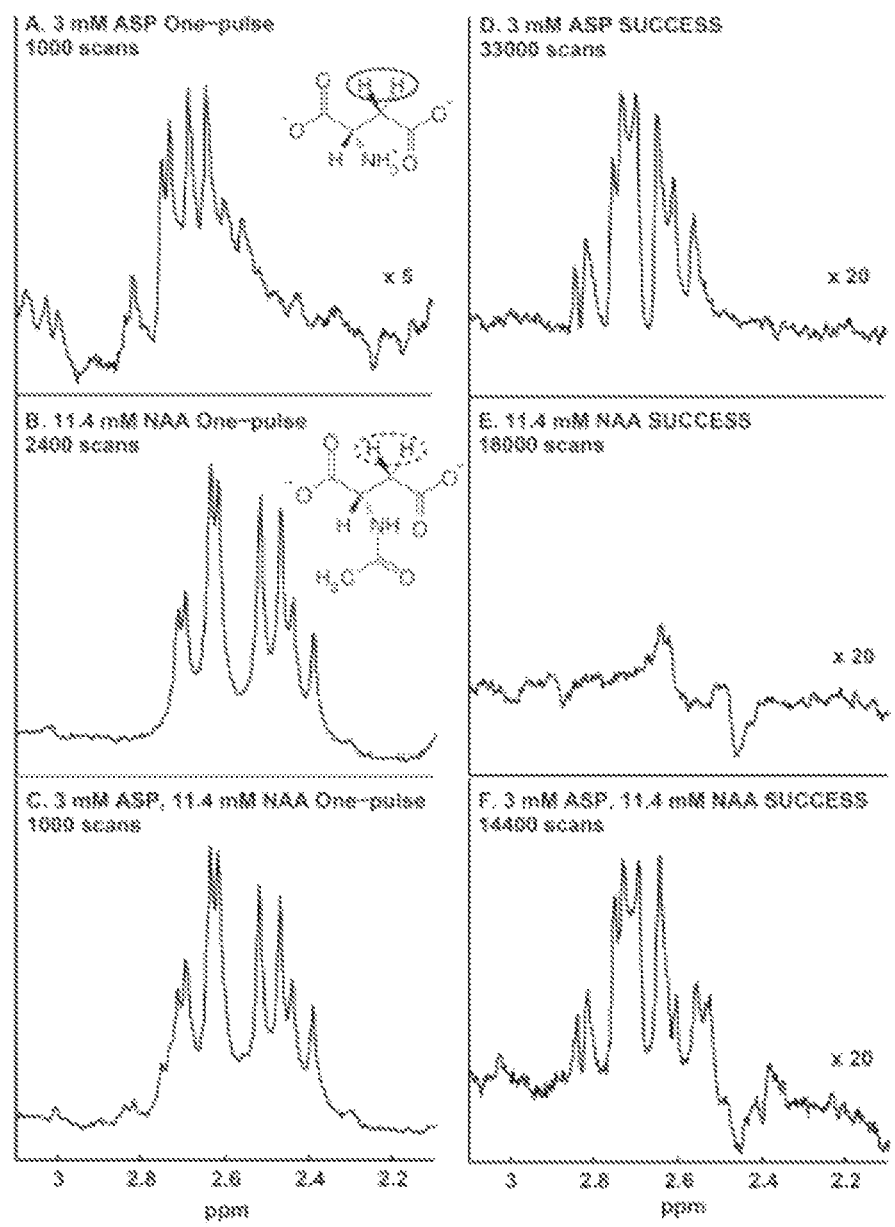
FIGS. 2A-2F illustrate measured NMR spectra for one-pulse (left column) and SUCCESS (right column) experiments performed on solutions of N-acetylaspartate (NAA), aspartate (Asp), and their mixture (intensity has been normalized by number of scans).

FIG. 2 shows measured NMR spectra for one-pulse (left column) and SUCCESS (right column) experiments performed on solutions of N-acetylaspartate (NAA), aspartate (Asp), and their mixture (intensity normalized by number of scans, N). The target protons for singlet formation are indicated on each molecule, with a solid oval for Asp indicating the targeted singlet, and a dashed oval for NAA indicating the undesired singlet. SUCCESS parameters were $\delta_0 = 2.71$ ppm, $\tau_1 = 9$ ms, $\tau_2 = 20.3$ ms, $\tau_3 = 11.5$ ms, $\tau_4 = 1$ s, and $v_n = 385$ Hz, line broadening 0.5 Hz. The one-pulse spectra of aspartate (FIG. 2A) and N-acetylaspartate (FIG. 2B) target spins each show strong second-order structure resulting from J couplings on the same order as the resonance frequency differences. Due to the significant structural and spectral similarity, in the one-pulse spectrum of FIG. 2C, the mixture only the aspartate peaks furthest downfield are evident. FIG. 2 further shows that a SUCCESS experiment targeting aspartate produces a spectrum with a similar shape to the one-pulse experiment when applied to the aspartate solution (FIG. 2D); but produces a weak signal when performed on N-acetylaspartate solution, with only residual magnetization remaining (FIG. 2E); and produces a spectrum dominated by aspartate when performed on the mixture (FIG. 2F).

The SUCCESS pulse sequence was tested on aspartate (Asp), which has a typical concentration of 3 mM in the brain. Asp contains a pair of protons, attached to a common carbon atom, with a long-lived singlet state that has previously been investigated (Vasos et al. (2009), *Proceedings of the National Academy of Sciences USA* 106: 18469-18473). Its acetylated form, N-acetylaspartate (NAA), is present in the brain at a concentration 3-6 times higher (Ross et al. (2001), *The Anatomical Record (New Anat.)* 265: 54-84; Cudalbu et al. (2005), *IEEE Proc. ProRISC Veldhoven, Netherlands*, 609-614; Sarchielli et al. (1999), *Brain* 122: 513-521; Birken et al. (1989), *Neuroscience and Biobehavioral Reviews* 13: 23-31). The geminal protons of interest in both molecules produce a second-order NMR spectral structure in the 2-3 ppm chemical shift range, with further splitting caused by a third nearby proton, whose peak appears near 4 ppm (FIG. 2A-B). In the control solutions, the singlet state lifetimes were measured, $T_S = 5.6 \pm 1$ s and $4.5 \pm 0.3$ s for Asp and NAA, respectively, and spin-lattice relaxation times, $T_1 = 1.3 \pm 0.2$ s and $0.99 \pm 0.06$ s for the proton pairs in Asp and NAA, respectively.

FIG. 2C shows that the measured one-pulse spectrum of the mixture (3.0 mM Asp, 11.4 mM NAA) is dominated by NAA, and only the Asp peaks near 2.8 ppm are visible. Using an appropriate set of pulse sequence parameters (see description of FIG. 2), a SUCCESS spectrum was obtained (FIG. 2E) with residual NAA magnetization of only 0.7% of its original integrated intensity in the control solution. The same SUCCESS sequence applied to the Asp control produced a spectrum that appeared similar to its one-pulse spectrum, but with an integrated signal strength about 15% of its the original intensity (FIG. 2D). Thus the result of the SUCCESS technique was an integrated contrast enhancement>20. Also, the aspartate peak intensities averaged 25% of their original strengths, and the peak contrast enhancement due to SUCCESS was >6 for all Asp peaks compared with NAA. Importantly, the SUCCESS spectrum of the mixture (FIG. 2F) appeared nearly identical to that of the Asp control, except for the weak residual NAA signal near 2.5 ppm. Moreover, the water signal was suppressed by a factor of 6.5.

SUCCESS pulse sequence was next applied to the amino acid threonine (Thr), which occurs at concentrations of around 500 µM in the brain (Wallwork et al. (1983), *Journal of Nutrition* 113: 47-54; Choi et al. (2006), *Magnetic Resonance in Medicine* 56: 660-665).

Figures 3A, 3B, 3C, 3D, 3E, 3F, 3G, 3H:
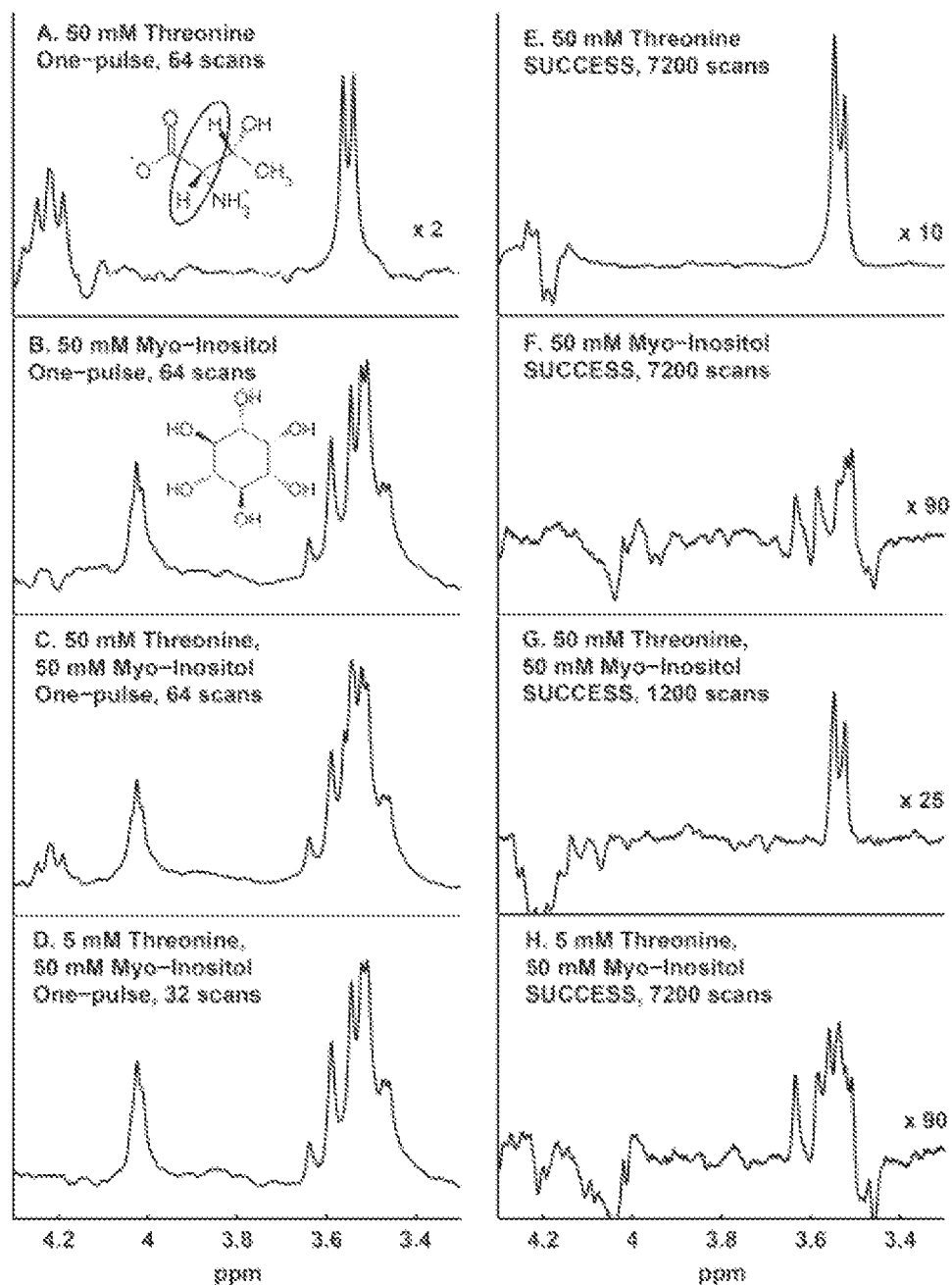
FIGS. 3A-3H illustrate measured NMR spectra for one pulse (left column) and SUCCESS (right column) experiments targeting threonine performed on solutions of myo-inositol, threonine, and two mixtures (intensity normalized by number of scans).

FIG. 3 shows measured NMR spectra for one pulse (left column) and SUCCESS (right column) experiments targeting threonine performed on solutions of myo-inositol, threonine, and two mixtures (intensity normalized by number of scans). The target protons for singlet formation on threonine are indicated with the solid oval. SUCCESS parameters were $\delta_0=3.87$ ppm, $\tau_1=40$ ms, $\tau_2=52$ ms, $\tau_3=1.85$ ms, $\tau_4=200$ ms, and $v_n=790$ Hz, except for frame (G), where $\tau_2=72$ ms and $\tau_3=4.8$ ms, line broadening 0.5 Hz. FIG. 3A shows that a one-pulse threonine spectrum of the target spins consists of a doublet and a multiplet. FIG. 3B shows that the one-pulse myo-inositol spectrum contains a number of peaks that overlap the threonine doublet, such that in a 1:1 mixture (see FIG. 3C), the threonine doublet is only partially resolved, and in a 10:1 mixture (see FIG. 3D), it is completely hidden. FIG. 3E shows that the SUCCESS sequence produces a threonine spectrum with the same doublet, but with an inverted multiplet due to interactions with the nearby methyl group. FIG. 3F shows that the myo-inositol SUCCESS spectrum with the same parameters is around 17 times weaker. FIG. 3G demonstrates that applying the SUCCESS pulse sequence to a 1:1 mixture effectively removes the myo-inositol signal. For a 10:1 mixture, the previously hidden threonine doublet is now partially resolved, as shown in FIG. 3H.

Threonine does not possess a pair of geminal protons, so the singlet is instead created on the vicinal protons attached to carbons two and three. The target proton peaks lie near 3.6 and 4.2 ppm (FIG. 3A), and the downfield proton is also coupled to a methyl group ($\delta=1:25$ ppm), which produces a multiplet splitting pattern. A singlet lifetime was measured, $T_S=2.0\pm0.3$ s and spin-lattice relaxation times, $T=2.0\pm0.2$ s and $2.2\pm0.1$ s for the vicinal protons. The singlet lifetime is shorter than $T_1$ because the interactions with the methyl group are strongly asymmetric with respect to the singlet spins. Note that interactions with the methyl group also lead to a measured SUCCESS spectrum (FIG. 3E) that is significantly different from the one-pulse spectrum (FIG. 3A): in particular, the 4.2 ppm peak is inverted.

The upfield target proton spectral peak in Thr is overlapped by peaks from the common metabolite i-inositol (spectrum shown in FIG. 3B), which occurs in the brain at concentrations of 4-12 mM (Ross et al. (2001), *The Anatomical Record* (*New Anat.*) 265: 54-84; Cudalbu et al. (2005), *IEEE Proc. ProRISC Veldhoven*, Netherlands 609-614). At a 10:1 myo-inositol:threonine concentration ratio, the myo-inositol peaks completely cover the upfield threonine peak and make it unresolvable in our spectrometer (FIG. 3D). Even at a 1:1 concentration ratio the threonine peak is only partially resolved (FIG. 3C). The optimized SUCCESS sequence suppressed the myo-inositol peaks to less than 0.7% of their original peak intensity, while it preserved 12% of the threonine peak signal intensity (FIG. 3E-F). The result was an average peak contrast enhancement of 17. Using integrated intensities, SUCCESS recovered 15.5% of threonine signal versus 0.3% for mnyo-inositol, to produce an integrated contrast enhancement of 60. When applied to the sample with equal concentrations of threonine and myo-inositol, the SUCCESS sequence reduced the intensity of myo-inositol so greatly that only the threonine peak was evident (FIG. 3G). When performed on the sample with a 10:1 concentration ratio, the resulting spectrum exhibited a threonine peak slightly more intense than myo-inositol, which allowed the previously hidden peaks to be identified (FIG. 3H). Full isolation of the threonine signal was not achieved in this case because the contrast enhancement was not great enough to overcome the large concentration ratio between threonine and myo-inositol. The water peak was suppressed by a factor of 32.

Finally, SUCCESS was applied to a mixture of glutamine (Gln) and glutamate (Glu), which play essential roles in neurotransmission. The typical glutamate concentration is twice that of glutamine in the brain (8 mM and 4 mM respectively) (Ross et al. (2001), *The Anatomical Record* (*New Anat.*) 265: 54-84; Cudalbu et al. (2005), *IEEE Proc. ProRISC Veldhoven*, Netherlands, 609-614; 1245-1250; Wallwork et al. (1983), *Journal of Nutrition* 113: 47-54; Schubert et al. (2004) 21: 1762-1771). These molecules have largely overlapping NMR spectra, which make molecule-specific measurements difficult (Mason et al. (1994), *Magnetic Resonance in Medicine* 32: 142-145), as well as similar chemical shifts and J-coupling strengths, which make the application of traditional quantum filters challenging. A number of spectral-editing techniques and quantum filters have been used to attack this problem (Thompson et al. (1998), *Magnetic Resonance in Medicine* 39: 762-771; Snyder et al. (2008), *Proceedings of the International Society for Magnetic Resonance in Medicine* 16: 1564; Thompson et al. (2001), *Magnetic Resonance in Medicine* 45: 955-965; Choi et al. (2006), *Magnetic Resonance in Medicine* 55: 997-1005; Hu et al. (2007), *Journal of Magnetic Resonance* 185: 204-213; Lee et al. (1995), *Magnetic Resonance in Medicine* 34: 253-259; Yang et al. (2008), *Magnetic Resonance in Medicine* 59:236-244), but none has become a routine and reliable way to measure glutamine concentration under physiologically relevant conditions.

FIGS. 4A-4F show measured NMR spectra for one pulse (left column) and SUCCESS (right column) experiments targeting glutamine performed on solutions of glutamate (Glu), glutamine (Gln), and their mixture (intensity normalized by number of scans, N). The protons for singlet formation are indicated on each structure, with a solid oval indicating the targeted singlet spins for glutamine, and a dashed oval indicating the undesired singlet for glutamate. SUCCESS parameters were $\delta_0=2.23$ ppm, $\tau_1\pm22$ ms, $\tau_2=15$ ms, $\tau_3=11.1$ ms, $\tau_4=500$ ms, and $v_n=385$ Hz, line broadening 1 Hz. The one pulse spectra of glutamine (FIG. 4A) and glutamate (FIG. 4B) both exhibit a complex structure with similar chemical shifts. In the spectrum of the mixture (FIG. 4C), the glutamine peaks near 2.4 ppm are partially resolved while those near 2.1 ppm are unresolved from those of glutamate. The SUCCESS spectrum of glutamine (FIG. 4D) is similar in structure to the one-pulse spectrum, whereas the SUCCESS spectrum of glutamate (FIG. 4E) contains only weak residual peaks. The SUCCESS spectrum of the mixture (FIG. 4F) is similar to that of glutamine alone, except for residual glutamate signal near 2.3 ppm.

Figures 4A, 4B, 4C, 4D, 4E, 4F:
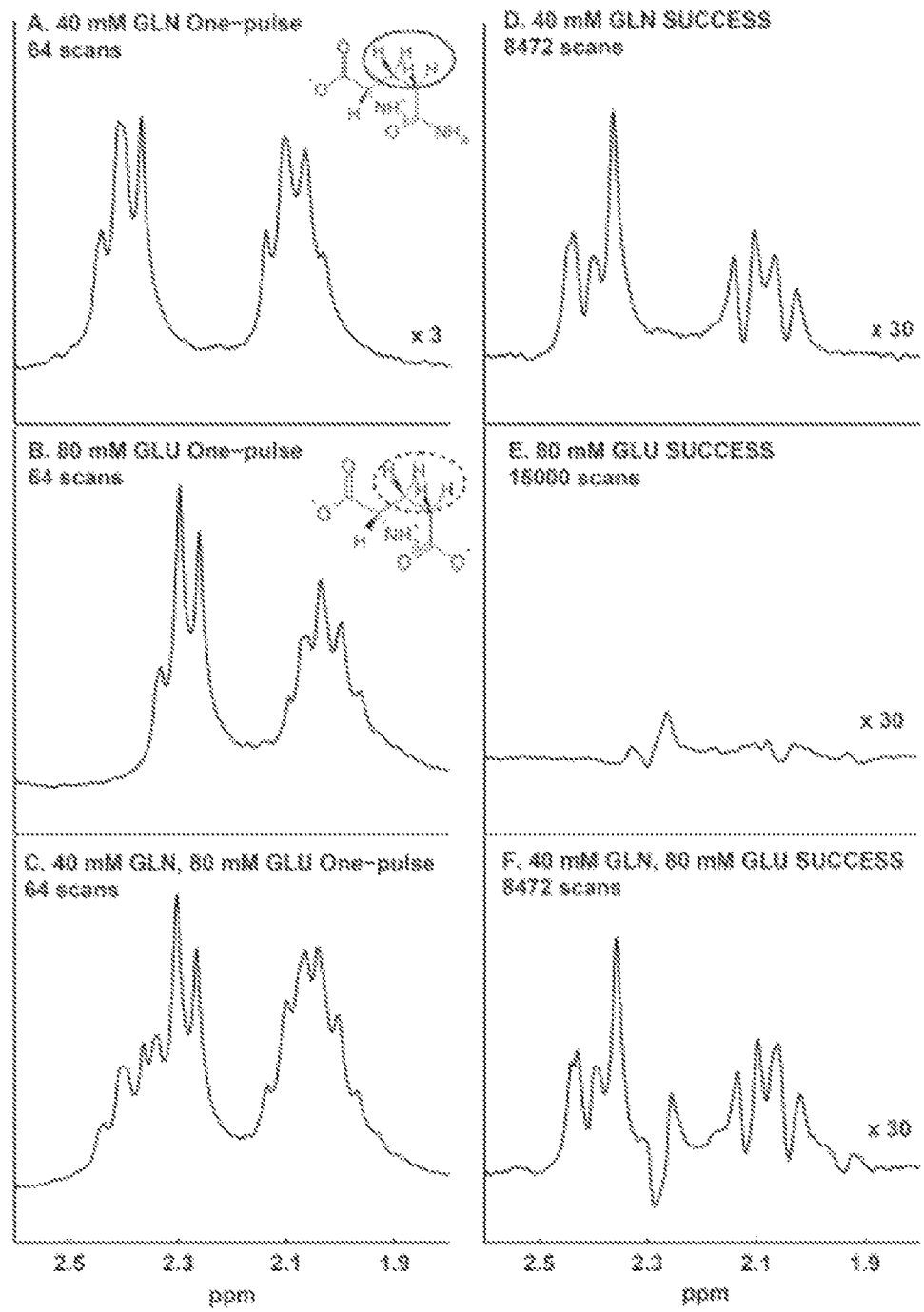
FIGS. 4A-4F illustrate measured NMR spectra for one pulse (left column) and SUCCESS (right column) experiments targeting glutamine performed on solutions of glutamate (Glu), glutamine (Gln), and their mixture (intensity normalized by number of scans).

Each molecule contains two methylene groups that can be viewed as pairs of strongly-coupled, unresolvable protons. A third lone proton couples to one of the methylene groups. The NMR spectra therefore exhibit a complex splitting pattern (FIG. 4A-B), with methylene group peaks between 1.8 and 2.6 ppm, and the lone proton peak at 3.7 ppm. A mixture of the two metabolites produces a spectrum with many poorly-resolved peaks, and the upfield methylene groups cannot be resolved at all (FIG. 4C). Each methylene group is already strongly mixed into singlet and triplet states, but the resulting singlets cannot be easily manipulated for utilization in the SUCCESS quantum filter. Instead, a four-spin singlet state can be created by mixing the triplet states of the two methylene groups. This singlet is preserved by RF spin locking, just like a two-spin singlet. It was found that the four-spin singlet can be selectively created depending on the pulse-sequence parameters. It still possesses spherical symmetry and passes through the polyhedral singlet filter, but it does not possess an extended lifetime. Lifetimes of 0.70±0.09 s and 0.80±0.1 s were measured for the four-spin singlet in glutamate and glutamine, respectively; and for the two methylene group triplet states $T_1 = 1.11 \pm 0.02$ s and $0.92 \pm 0.02$ s was measured for glutamate, and $1.24 \pm 0.05$ s and $1.01 \pm 0.04$ for glutamine. Since the four-spin singlet state is made up of two triplet states that can undergo relaxation, the singlet state lifetimes were shorter than the spin-lattice lifetimes of their constituent methylene groups. Nevertheless, it was found that the four-spin singlet lifetime is sufficiently long for SUCCESS to be effective in glutamine and glutamate.

The SUCCESS pulse sequence delays were experimentally optimized to obtain high contrast for glutamine. The measured SUCCESS spectrum for glutamine (FIG. 4D) was similar to the one-pulse spectrum (FIG. 4A), whereas the SUCCESS spectrum for glutamate consisted only of a single, very weak peak (FIG. 4E) compared to the intense multi-peak one-pulse spectrum (FIG. 4B). The SUCCESS spectrum of the Gln/Glu mixture (FIG. 4F) appeared similar to that of glutamine with the small residual glutamate peak at 2.3 ppm. This residual peak did not interfere with any glutamine peaks, and so the positions of the upfield methylene peaks of glutamine were now measureable. The glutamate signal was suppressed so that only 0.5% of its original integrated intensity remained, while 5.1% of the glutamine integrated signal intensity was recovered, resulting in a Gln/Glu contrast enhancement of 10 due to SUCCESS. The peak intensities of glutamate were at most 0.86% the original levels, while those of glutamine averaged 5.7% of the original intensity, thereby producing peak Gln/Glu contrast enhancements between 3 and 7. The water signal was suppressed by a factor of 13.

Figures 6A, 6B, 6C:
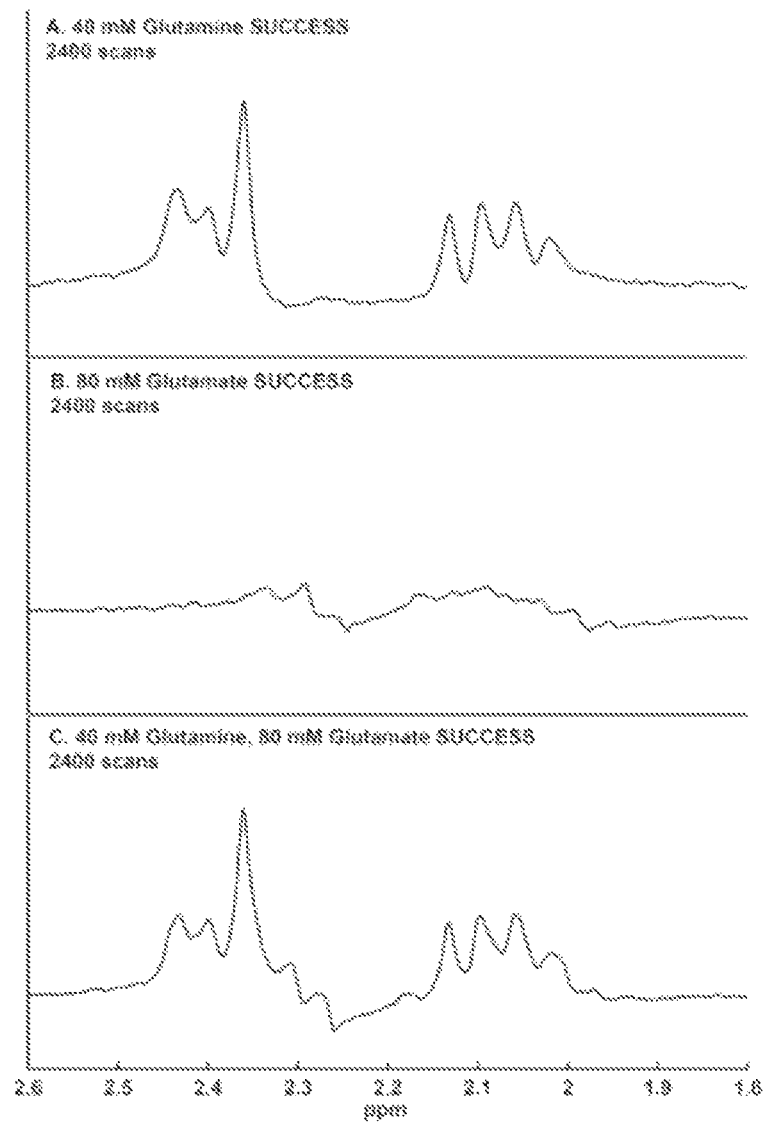
FIGS. 6A-C illustrate measured NMR spectra for SUCCESS experiments targeting glutamine performed on solutions of glutamate, glutamine, and their mixture, in which the RF transmit frequency was shifted away from the average resonance frequency by 40 Hz.

The transmitter frequency can also be used as a parameter to optimize SUCCESS contrast. It was found that higher signal from glutamine could be obtained by moving the transmitter frequency approximately 40 Hz upfield from the average value, to $\delta_{av} = 2.05$ ppm, for the whole sequence and by applying a different set of delays. This frequency adjustment created the same level of peak contrast while preserving 15% of the glutamine peak signal intensity (FIG. 6A-C). Water suppression was also higher, with a peak 38 times weaker than in a one-pulse scan.

FIG. 6A-C shows measured NMR spectra for SUCCESS experiments targeting glutamine performed on solutions of glutamate, glutamine, and their mixture, in which the RF transmit frequency was shifted away from the average resonance frequency by 40 Hz, to $\delta_0 = 2.05$ ppm. Delays were $\tau_1 = 18$ ms, $\tau_2 = 9$ ms, $\tau_3 = 4.5$ ms, $\tau_4 = 100$ ms, and $v_n = 385$ Hz, line broadening was 1 Hz, and 2400 scans were performed for each sample. Intensity was normalized by the number of scans. The SUCCESS spectrum of glutamine (FIG. 6A) is much stronger than that of glutamine (FIG. 6B), and in the spectrum of the mixture (FIG. 6C), the glutamine signal dominates.

While SUCCESS is designed to be effective at removing background signals in the same spectral region as a target, it is less effective at removing signals spectrally far from the target. Measurements on the suppression of the water peak in buffer solution alone were performed, using parameters for glutamine, and found that the SUCCESS filter has a bandwidth of approximately 250 Hz. Outside this bandwidth, background suppression varies, which may lead to significant differences in water suppression for different metabolites. It may be possible to develop a more broadband filter using magnetic gradients in lieu of the phase cycle to act as a dephasing mechanism for spins not in the singlet state.

What is claimed is:

1. A method comprising:
    selectively creating a nuclear spin singlet state in a target molecule, so as to detect presence of the target molecule within a sample, wherein the sample contains a mixture of molecules and includes at least some background molecules that are different from the target molecule; and
    preserving spin polarization of the singlet state while saturating the spin magnetizations of background molecules, so as to suppress spectroscopic signals from the background molecules and to enhance spectroscopic contrast between the target molecule and the background molecules,
    wherein the act of selectively creating the nuclear spin singlet state comprises:
        applying to the target molecule a sequence of pulses having parameters that are optimized so as to achieve the desired nuclear spin singlet state in the target molecule while minimizing singlet nature of the nuclear spin states of the background molecules.

2. The method of claim 1, further comprising converting the spin polarization of the singlet state back to transverse magnetization for signal readout, by controllably applying RF (radiofrequency) pulses.

3. The method of claim 1, wherein the act of preserving spin polarization of the singlet state while saturating spin magnetization of the background molecules comprises: applying a substantially continuous spin-locking RF field.

4. The method of claim 3, further comprising applying the spin-locking RF field at an average resonance frequency of coupled protons in the target molecule.

5. The method of claim 3, further comprising applying the spin-locking RF field at a frequency other than an average resonant frequency of coupled protons in the target molecule, so as to further enhance spectroscopic signals from the target molecule.

6. The method of claim 1, wherein the act of saturating spin magnetization of background molecules comprises:
    using a polyhedral, spherically symmetric phase cycle that substantially removes non-singlet signals.

7. The method of claim 1, wherein the target molecule is one of: aspartate, threonine, and glutamine.

8. The method of claim 7, wherein the background molecules comprise at least one of: N-acetylaspartate, myo-inositol, and glutamate.

9. The method of claim 1, wherein the sequence of pulses is a pulse sequence depicted in FIG. 1A, 1B, 5A or 5B.

10. An NMR (nuclear magnetic resonance) system, comprising:

an NMR transceiver including an RF generator configured to generate a sequence of RF fields that have controllable parameters; and a controller configured to generate and optionally relay a set of instructions to the transceiver to controllably apply the RF field sequence to a sample, so as to selectively create a nuclear spin singlet state in a target molecule, then preserve spin polarization of the singlet state while saturating the spin magnetizations of background molecules within the sample, thereby suppressing spectroscopic signals from the background molecules and enhancing spectroscopic contrast between the target and background molecules, wherein the controller is further configured to optimize the parameters of the RF field sequence so as to convert the spin polarization of the singlet state back to transverse magnetization, for signal readout from the target molecule.

11. The system of claim 10, wherein the RF field sequence includes a spin-locking RF field that is resonant with the spins and is substantially continuous, and wherein the spin-locking RF field is applied after the nuclear spin singlet state has been selectively created in the target molecule, thereby preserving spin polarization of the singlet state while saturating spin magnetizations of the background molecules.

12. The system of claim 10, wherein the target molecule is aspartic acid and the background molecules comprise N-acetylaspartic acid, and wherein the optimized parameters of the RF field sequence comprise:
transmit frequency v=385 Hz;
chemical shift δav=2.71 ppm; and
singlet creation delay times $\tau 1$, $\tau 2$ and $\tau 3$ and relaxation delay time $\tau 4$,
where $\tau 1$=9 ms (milliseconds), $\tau_2$=10.3 ms, $\tau_3$=11.5 ms, and $\tau_4$=1 sec.

13. The system of claim 10, wherein the target molecule is glutamine and the background molecules comprise glutamate, and wherein the optimized parameters of the RF field sequence comprise:
transmit frequency v=385 Hz;
chemical shift $\delta_{av}$=2.23 ppm; and
singlet creation delay times $\tau_1$, $\tau_2$ and $\tau_3$, and relaxation delay time $\tau_4$;
where $\tau_1$=22 ms (milliseconds), $\tau_2$=15 ms, $\tau_3$=11.1 ms, and $\tau_4$=500 ms.

14. The system of claim 10, wherein the target molecule is threonine and the background molecules comprise myo-inositol, and wherein the optimized parameters of the RF field sequence comprise:
Transmit frequency v=790 Hz;
chemical shift $\delta_{av}$=3.87 ppm; and
singlet creation delay times $\tau_1$, $\tau_2$ and $\tau_3$, and relaxation delay time $\tau_4$;
where $\tau_1$=40 ms (milliseconds), $\tau_2$=52 ms, $\tau_3$=1.85 ms, and $\tau_4$=200 ms.

15. The system of claim 10, wherein the RF sequence is a pulse sequence depicted in FIG. 1A, 1B, 5A or 5B.

16. A method comprising:
selectively creating a nuclear spin singlet state in a target molecule, so as to detect presence of the target molecule within a sample, wherein the sample contains a mixture of molecules and includes at least some background molecules that are different from the target molecule; and
preserving spin polarization of the singlet state while saturating the spin magnetizations of background molecules, so as to suppress spectroscopic signals from the background molecules and to enhance spectroscopic contrast between the target molecule and the background molecules,
wherein an NMR spectrum of the target molecule is similar to, and substantially overlaps with, an NMR spectrum of the background molecules.

17. The method of claim 16, further comprising converting the spin polarization of the singlet state back to transverse magnetization for signal readout, by controllably applying RF (radiofrequency) pulses.

18. The method of claim 16, wherein the act of preserving spin polarization of the singlet state while saturating spin magnetization of the background molecules comprises:
applying a substantially continuous spin-locking RF field.

19. The method of claim 18, further comprising applying the spin-locking RF field at an average resonance frequency of coupled protons in the target molecule.

20. The method of claim 19, wherein the RF field sequence includes a spin-locking RF field that is resonant with the spins and is substantially continuous, and wherein the spin-locking RF field is applied after the nuclear spin singlet state has been selectively created in the target molecule, thereby preserving spin polarization of the singlet state while saturating spin magnetizations of the background molecules.

21. The method of claim 19, wherein the target molecule is aspartic acid and the background molecules comprise N-acetylaspartic acid, and wherein the optimized parameters of the RF field sequence comprise:
transmit frequency v=385 Hz;
chemical shift δav=2.71 ppm; and
singlet creation delay times $\tau 1$, $\tau 2$ and $\tau 3$ and relaxation delay time $\tau 4$,
where $\tau 1$=9 ms (milliseconds), $\tau_2$=10.3 ms, $\tau_3$=11.5 ms, and $\tau_4$=1 sec.

22. The method of claim 19, wherein the target molecule is glutamine and the background molecules comprise glutamate, and wherein the optimized parameters of the RF field sequence comprise:
transmit frequency v=385 Hz;
chemical shift $\delta_{av}$=2.23 ppm; and
singlet creation delay times $\tau_1$, $\tau_2$ and $\tau_3$, and relaxation delay time $\tau_4$;
where $\tau_1$=22 ms (milliseconds), $\tau_2$=15 ms, $\tau_3$=11.1 ms, and $\tau_4$=500 ms.

23. The method of claim 19, wherein the target molecule is threonine and the background molecules comprise myo-inositol, and wherein the optimized parameters of the RF field sequence comprise:
Transmit frequency v=790 Hz;
chemical shift $\delta_{av}$=3.87 ppm; and
singlet creation delay times $\tau_1$, $\tau_2$ and $\tau_3$, and relaxation delay time $\tau_4$;
where $\tau_1$=40 ms (milliseconds), $\tau_2$=52 ms, $\tau_3$=1.85 ms, and $\tau_4$=200 ms.

24. The method of claim 19, wherein the RF sequence is a pulse sequence depicted in FIG. 1A, 1B, 5A or 5B.

25. The method of claim 18, further comprising applying the spin-locking RF field at a frequency other than an average resonant frequency of coupled protons in the target molecule, so as to further enhance spectroscopic signals from the target molecule.

26. The method of claim 16, wherein the act of saturating spin magnetization of background molecules comprises:
using a polyhedral, spherically symmetric phase cycle that substantially removes non-singlet signals.

27. The method of claim 16, wherein the target molecule is one of: aspartate, threonine, and glutamine.

28. The method of claim 16, wherein the background molecules comprise at least one of: N-acetylaspartate, myo-inositol, and glutamate.

29. An NMR (nuclear magnetic resonance) system, comprising:
- an NMR transceiver including an RF generator configured to generate a sequence of RF fields that have controllable parameters; and
- a controller configured to generate and optionally relay a set of instructions to the transceiver to controllably apply the RF field sequence to a sample, so as to selectively create a nuclear spin singlet state in a target molecule, then preserve spin polarization of the singlet state while saturating the spin magnetizations of background molecules within the sample, thereby suppressing spectroscopic signals from the background molecules and enhancing spectroscopic contrast between the target and background molecules,
- wherein the NMR spectrum of the target molecule is similar to, and substantially overlaps with, the NMR spectrum of the background molecules.

* * * * *